United States Patent
Jiang et al.

(10) Patent No.: US 9,562,242 B2
(45) Date of Patent: Feb. 7, 2017

(54) METHOD FOR REUSING WATER IN FERMENTED BUTANEDIOIC ACID SEPARATION PROCESS

(75) Inventors: Min Jiang, Nanjing (CN); Min Zhang, Nanjing (CN); Jiangfeng Ma, Nanjing (CN); Hao Wu, Nanjing (CN); Liya Liang, Nanjing (CN); Rongming Liu, Nanjing (CN); Guangming Wang, Nanjing (CN); Ping Wei, Nanjing (CN)

(73) Assignee: NANJING UNIVERSITY OF TECHNOLOGY, Nanjing, Jiangsu (CN)

( * ) Notice: Subject to any disclaimer, the term of this patent is extended or adjusted under 35 U.S.C. 154(b) by 62 days.

(21) Appl. No.: 14/344,608

(22) PCT Filed: Sep. 13, 2012

(86) PCT No.: PCT/CN2012/081350
§ 371 (c)(1),
(2), (4) Date: Mar. 13, 2014

(87) PCT Pub. No.: WO2013/037298
PCT Pub. Date: Mar. 21, 2013

(65) Prior Publication Data
US 2014/0349356 A1  Nov. 27, 2014

(30) Foreign Application Priority Data
Sep. 13, 2011 (CN) .......................... 2011 1 0269332

(51) Int. Cl.
| | | |
|---|---|---|
| *C12P 7/46* | (2006.01) | |
| *C07C 51/41* | (2006.01) | |
| *C07C 51/43* | (2006.01) | |
| *C07C 51/44* | (2006.01) | |

(52) U.S. Cl.
CPC ............... *C12P 7/46* (2013.01); *C07C 51/412* (2013.01); *C07C 51/43* (2013.01); *C07C 51/44* (2013.01)

(58) Field of Classification Search
CPC ......... C12M 47/10; Y02E 50/16; Y02E 50/17; Y02E 50/343; Y02E 50/10; Y02E 50/30; Y02E 50/32; Y02E 50/13; C12P 7/10; C12P 2201/00; C12P 2203/00; C07C 55/10; C13K 1/02; C13K 1/06; C08B 1/00; C08B 15/00; C08B 1/003
USPC .......................................................... 435/145
See application file for complete search history.

(56) References Cited

FOREIGN PATENT DOCUMENTS

| CN | 101029319 | * | 9/2007 | .............. C12P 13/14 |
|---|---|---|---|---|
| CN | 101475464 | * | 7/2009 | .............. C07C 55/10 |
| CN | 101792778 | * | 8/2010 | ................ C12P 7/46 |

OTHER PUBLICATIONS

Lin et al. Novel resin-based vacuum distillation-crystallisation method for recovery of succinic acid crystals from fermentation broths. Green Chem. 2010;12:666-671.*

* cited by examiner

*Primary Examiner* — Lynn Y Fan
(74) *Attorney, Agent, or Firm* — BEI & Ocean; George G. Wang

(57) ABSTRACT

This invention belongs to the field of biochemical engineering and relates to a method of cyclic utilization of water during separation of succinic acid made by fermentation. This invention uses water from separation process for aerobic growth of *E. coli* AFP111 and production of succinic acid by anaerobic fermentation, obtaining final succinic acid concentration of 55 g/L and yield of 91.6%. Compared with results of fermentation using culture medium prepared from tap water, succinic acid concentration and productivity increased by 8.5% and 8.46%, respectively. An outstanding advantage of this invention is recovery and utilization of evaporated water during separation of succinic acid, realizing cyclic use of water during industrial production of succinic acid, which is an environment-friendly process. Also, as evaporated water generated during separation of succinic acid contains small amount of organic acids such as acetic acid and formic acid, if this water is used for aerobic growth of thalli, the small amount of organic acids contained therein can be used as gluconeogenesis carbon source, improving activity of some key enzymes in cell and favoring succinic acid production by anaerobic fermentation of thalli.

2 Claims, 1 Drawing Sheet

METHOD FOR REUSING WATER IN FERMENTED BUTANEDIOIC ACID SEPARATION PROCESS

FIELD OF THE INVENTION

This invention belongs to the field of biochemical engineering and relates to a method of cyclic utilization of water from fermentive succinic acid separation process, particularly, a method of recovery and reutilization of industrial evaporated water and steam condensate for enhanced biosuccinic acid production,

BACKGROUND OF THIS INVENTION

Succinic acid, also referred to as amber acid, is a dicarboxylic acid. It is an important $C_4$ platform compound, which can be used for surfactant, detergent additive, and foaming agent etc. As ion chelating agent, it can be used for the electroplating industry. In the food service industry, it can be used as acidifier, pH modifier, flavor substance, and foodstuff modifier. It can also be used for production of medicine, antibiotics, amino acid, and vitamin.

There are two main methods for succinic acid production: chemical synthesis and micro-organism fermentation. The chemical method normally adopts butane and maleic anhydride for production by electrolysis. This method causes serious pollution, and has low conversion rate and high costs, seriously limiting the development of succinic acid market. Regarding production of succinic acid by microorganism fermentation, since supply of raw materials is wide and cheap, this process is environment-friendly and has light pollution, and fixed $CO_2$ can be absorbed during fermentation, thus effectively mitigating greenhouse effect, this method is a new way of utilization of the greenhouse gas of $CO_2$ and has become a hot point of research in recent years. Since *Escherichia coli* has clear heredity background; is easy to operate, adjust, control, and cultivate; has simple requirements; and grows fast, it has been widely used in research in recent years, to obtain excellent strain that produces succinic acid.

The fermentation liquid that produces succinic acid by micro-organism fermentation needs to undergo pre-filtering, ultrafiltration, nano-filtration, concentration, and crystallization, to finally yield disodium succinate or succinic acid. During concentration of fermentation liquid, large amount of evaporated water and steam condensate is obtained. This evaporated water contains small amount of organic acids such as acetic acid and formic acid. Use of this water for aerobic cultivation of cells can promote cell metabolic capability by improving activity of some key enzymes in the cell, so that acid production performance of thalli is improved. Steam condensate generated during separation of succinic acid fermentation liquid does not contain organic acid or metallic ion, so that when used for thalli fermentation, osmotic pressure of the fermentation system will not increase. This condensate can be used for anaerobic fermentation stage of cells.

SUMMARY OF THE INVENTION

The technical issue of this invention is a method of succinic acid production by fermentation, which uses evaporated water and steam condensate generated during separation of succinic acid, so as to solve the problem of recovery and utilization of industrial evaporated water and steam condensate, and further increase succinic acid concentration and productivity and To realize the objectives of this invention, the technical scheme used is described below.

A method of cyclic utilization of water during separation of succinic acid produced by fermentation, comprising steps of aerobic cultivation of seed, succinic acid production by anaerobic fermentation, and separation of succinic acid, wherein evaporated water or steam condensate recovered during the step of separation of succinic acid is used to prepare culture medium of aerobic cultivation of seed and culture medium of anaerobic fermentation of thalli, and steam condensate recovered during the step of separation of succinic acid is used to prepare culture medium of acid production by anaerobic fermentation, to realize cyclic utilization of water.

Said evaporated water or steam condensate recovered during the step of separation of succinic acid is generated during vacuum evaporation and concentration of the succinic acid fermentation liquid obtained at end of the step of acid production by anaerobic fermentation, following pre-filtering of said fermentation liquid, ultrafiltration under acidic condition, nano-filtration under acidic condition, and repeated nano-filtration under neutral condition. This evaporated water contains small amount of organic acids such as acetic acid and formic acid. This steam condensate does not contain organic acid and its compositions are the same as those of distilled water.

Further, the method of aerobic cultivation of seed described in this invention shall be understood as any seed aerobic cultivation method in existing technology making use of *Escherichia coli* that produces succinic acid. In this invention, *Escherichia coli* AFP111 thalli is placed in a conical flask for aerobic cultivation, using LB seed culture medium. In particular, a single colony is taken and transferred to a 5 mL test tube, which is placed in a mechanical shaker at 37° C. and 200 r/min for overnight activation. Then, according to inoculum size of 1%, transfer this to a 500 mL conical flask containing 50 mL of liquid for aerobic cultivation. Add 30 mg/L of kanamycin and chloromycetin, and place the flask in a mechanical shaker at 37° C. and 200 r/min for about 8 h of cultivation, to be used as seed liquid.

Further, the method of acid production by anaerobic fermentation described in this invention shall be understood as any anaerobic fermentation acid production method in existing technology making use of *Escherichia coli* that produces succinic acid. In this invention, shake-flask culture can be adopted. For example, subject the seed liquid obtained from aerobic cultivation to centrifugation at 4° C. and 8000 r/min for 10 min, to obtain bacterial mud. After washing this mud even, transfer it to a 100 mL serum bottle containing 30 mL of liquid, so that initial concentration of thalli is about 10 ($OD_{600}$) and initial concentration of glucose is 20 g/L. Next, connect $CO_2$ gas that has been filtered and sterilized for 2 min to ensure anaerobic environment in the serum bottle. Place it at 37° C. and 200 r/min for anaerobic fermentation. Fermenter culture can also be adopted. For example, according to inoculum size of 5%, transfer seed liquid obtained from anaerobic fermentation of thalli to a 7 L fermenter (BioFlo 110 fermenter; New Brunswick Scientific Co., Edison, N.J.) containing 4 L of fermentation medium. Add filtered and sterilized $VB_1$ and biotin to final concentration of 20 mg/L and 2 mg/L respectively. Add chloromycetin to 30 mg/L and kanamycin to 30 mg/L. Maintain fermentation temperature at 37° C. and use NaOH to adjust pH value to 7.0. At start of fermentation, connect 0.5 L/min of air and stir at 300 r/min. When thalli concentration exceeds 5 ($OD_{600}$), start to connect oxygen enriched air. When thalli concentration reaches 15 ($OD_{600}$), start to use glucose makeup at limited speed to control thalli specific growth rate at about 0.07 $h^{-1}$, till thalli concentration reaches 30 ($OD_{600}$), at which time connection of $CO_2$ shall start, converting to anaerobic fermentation.

Further, the method of separation of succinic acid described in this invention shall be understood as any succinic acid separation method in existing technology used for fermentation liquid obtained from fermentation of *Escherichia coli* that produces succinic acid. In this invention, the steps of separation are as follows:

(1) Pre-filtering: pre-filtering, in particular micro-filtration, of succinic acid fermentation liquid is carried out to remove thalli and solid particles.

(2) Acidic ultrafiltration: adjust filtrate pH value to 4.0~6.0 for ultrafiltration, to remove biomacromolecules such as proteins. Operating temperature is 25~40° C. and operating pressure is 0.2~4.0 MPa. Collect ultrafiltration filtrate.

(3) Acidic nano-filtration: adjust ultrafiltration filtrate pH value to 3.0~4.0 for nano-filtration, to remove pigments, multi-valence inorganic ions, and unconsumed substrate. Operating temperature is 25~40° C. and operating pressure is 1.0~2.5 MPa. Collect nano-filtration filtrate.

(4) Neutral nano-filtration: adjust pH value of nano-filtration filtrate containing succinic acid to 6.0~7.0 and repeat nano-filtration to remove byproducts such as formic acid and acetic acid, as well as mono-valence ions. Operating temperature is 25~40° C. and operating pressure is 0.2~4.0 MPa. Collect nano-filtration trapped liquid and realize pre-concentration.

(5) Concentration by evaporation: Perform concentration of nano-filtration trapped liquid by vacuum evaporation. Operating temperature is 65~75° C. and operating pressure is −0.08~0.1 MPa. Concentrated liquid is obtained, as well as large amount of evaporated water and steam condensate. Volume of evaporated water obtained is about 5/6 of the volume of succinic acid fermentation liquid. Keep the concentrated liquid at 50~70° C. and use sodium carbonate to adjust pH value of the concentrated liquid to 6.8. Next, perform crystallization by cooling, and drying, to obtain disodium succinate.

Beneficial effects of this invention:

1. This invention replaces distilled water, pure water, or tap water used for preparation of culture medium in existing technology by evaporated water and steam condensate generated during separation of succinic acid fermentation liquid, for cultivation and fermentation of *Escherichia coli*, realizing recovery and utilization of industrial wastewater and environment-friendly process. At the same time, as evaporated water generated during separation of succinic acid contains small amount of organic acids such as acetic acid and formic acid, if this water is used for aerobic cultivation of *Escherichia coli*, the organic acids contained therein can be used as gluconeogenesis carbon source, improving activity of some key enzymes in cell and favoring acid production by anaerobic fermentation of thalli. On the other hand, use of steam condensate to prepare culture medium has no adverse effect.

2. In step (3) of this invention, evaporated water generated during separation of succinic acid is used to prepare fermentation culture medium. At end of fermentation, concentration of succinic acid can reach 55 g/L and the yield can reach 91.6%. Compared with results of fermentation using culture medium prepared from tap water, succinic acid concentration has increased by 8.5% and production intensity has increased by 8.46%.

DETAILED DESCRIPTION OF PREFERRED EMBODIMENTS

Figure 1:
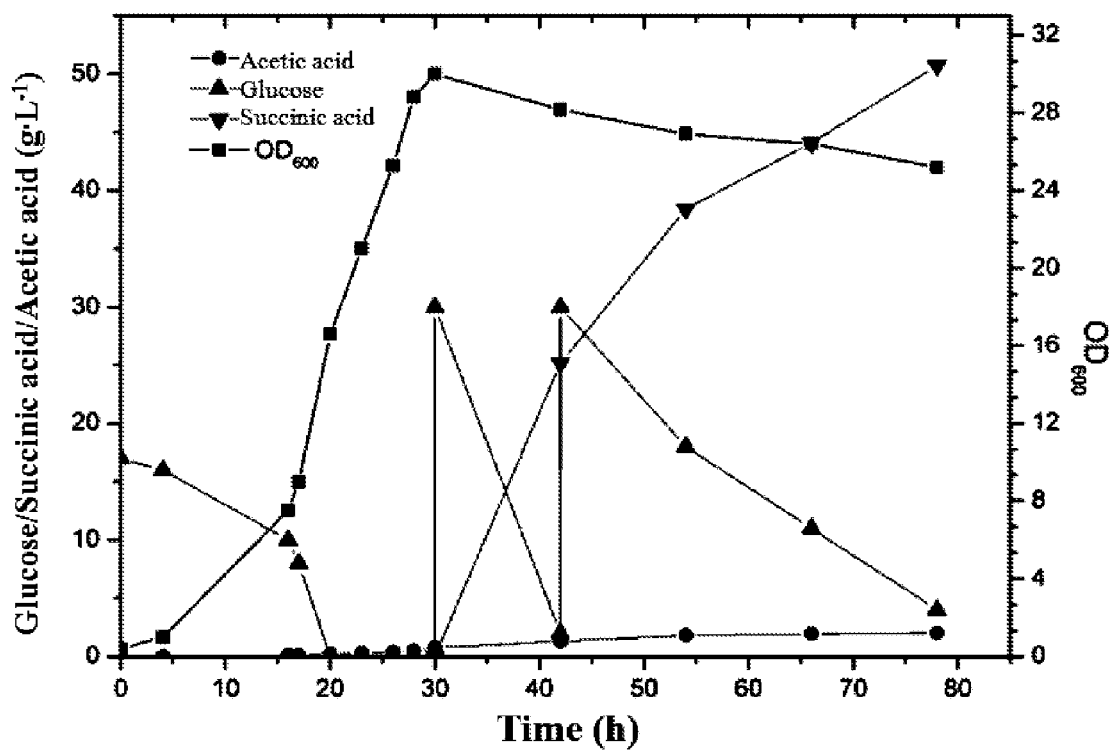
FIG. 1 Curves of change of concentrations of glucose, succinic acid, acetic acid, and thalli during cultivation of *Escherichia coli* AFP111 in JSM fermentation culture medium prepared from tap water.

Culture media described in this invention:

(1) LB seed liquid culture medium: 10 g/L of peptone, 5 g/L of yeast extract, and 10 g/L of NaCl.

(2) JSM fermentation culture medium: 3.0 g/L of citric acid, 3.00 g/L of $Na_2HPO_4 \cdot 7H_2O$, 8.00 g/L of $KH_2PO_4$, 8.00 g/L of $(NH_4)_2HPO_4$, 0.2 g/L of $NH_4Cl$, 0.75 g/L of $(NH4)_2SO_4$, 1.00 g/L of $MgSO4 \cdot 7H_2O$, 10.0 mg/L of $CaCl_2 \cdot 2H_2O$, 0.5 g/L of $ZnSO_4 \cdot 7H_2O$, 0.25 mg/L of $CuCl_2 \cdot 2H_2O$, 2.5 mg/L of $MnSO_4 \cdot H_2O$, 1.75 mg/L of $CoCl_2 \cdot 6H_2O$, 0.12 mg/L of $H_3BO_3$, 1.77 mg/L of $Al_2(SO_4)_3 \cdot xH_2O$, 0.5 mg/L of $Na_2MoO_4 \cdot 2H_2O$, 16.1 mg/L of ferric citrate, 20 mg/L of $VB_1$, and 2 mg/L of biotin.

Recombined *Escherichia coli* AFP111 used by this invention has two sources:

(1) Biotechnol Bioeng, 2001, 74:89~95. This applicant first found this literature about this biomaterial, and then contacted the author, i.e. professor David P. Cl!rk of Chicago University of USA, by a mail to request bestowal of this biomaterial. In this way, this applicant obtained this biomaterial free of charge. This applicant promises to release this biomaterial to the public within 20 years since this date of application.

(2) This biomaterial is also disclosed and authorized in a Chinese patent (application No.: 96198547.X; date of application: 1996.10.31; date of authorization: 2003.1.1; authorization publication No.: CN1097632C).

Organic acids analysis method used by this invention is:

High performance liquid chromatography (HPLC): HPLC system high performance liquid chromatograph, Waters HPLC C2010 workstation, chromatographic column (Prevail organic acid column 250 mm×4.6 mm); ultraviolet detection wavelength: 215 nm; flowing speed: 1 mL/min; amount of intake: 20 μL; mobile phase: 25 mmol/L $KH_2PO_4$; pH 2.5; column temperature: room temperature The following preferred embodiments provide detailed description of this invention but do not limit this invention.

Embodiment 1

Aerobic cultivation of seed: Transfer germ seed from freezing storage tube to a test tube, and place this test tube in a mechanical shaker for overnight activation. Then, according to inoculum size of 1%, transfer the content of this test tube to a 500 mL conical flask containing 50 mL of seed culture medium. At temperature of 37° C. and shaker speed of 200 r/min, cultivate for 8 h.

Succinic acid production by anaerobic fermentation in shake-flask: Carry out centrifugation of cultivated seed liquid at 4° C. and 8000 r/min for 10 min to obtain bacterial mud. Use sterilized water to wash this mud even and then transfer it to a 100 mL serum bottle containing 30 mL of liquid for anaerobic cultivation, so that initial concentration of thalli is 10 ($OD_{600}$). Then, connect $CO_2$ gas that has been filtered and sterilized for 2 min. Place it in a mechanical shaker at 37° C. and 200 r/min for anaerobic fermentation.

Preparation of evaporated water and steam condensate is synchronized with separation of succinic acid. Particular method is:

(1) Pre-filtering: pre-filtering, in particular micro-filtration, of succinic acid fermentation liquid is carried out to remove thalli and solid particles.

(2) Acidic ultrafiltration: adjust filtrate pH value to 4.0 for ultrafiltration, to remove biomacromolecules such as proteins. Operating temperature is 25° C. and operating pressure is 0.2 MPa. Collect ultrafiltration filtrate.

(3) Acidic nano-filtration: adjust ultrafiltration filtrate pH value to 3.0 for nano-filtration, to remove pigments, multivalence inorganic ions, and unconsumed substrate. Operating temperature is 25° C. and operating pressure is 1.0 MPa. Collect nano-filtration filtrate.

(4) Neutral nano-filtration: adjust pH value of nano-filtration filtrate containing succinic acid to 6.0 and repeat nano-filtration to remove byproducts such as formic acid and acetic acid, as well as mono-valence ions. Operating temperature is 25° C. and operating pressure is 0.2 MPa. Collect nano-filtration trapped liquid and realize pre-concentration.

(5) Concentration by evaporation: Perform concentration of nano-filtration trapped liquid by vacuum evaporation. Operating temperature is 65° C. and operating pressure is −0.08 MPa. Concentrated liquid is obtained, as well as large amount of evaporated water and steam condensate. Volume of evaporated water obtained is about ⅚ of the volume of succinic acid fermentation liquid. Keep the concentrated liquid at 50° C. and use sodium carbonate to adjust pH value of the concentrated liquid to 6.8. Next, perform crystallization by cooling, and drying, to obtain disodium succinate.

Detection of substances in evaporated water and steam condensate: HPLC has been used. Detection results: formic acid content in evaporated water is 1.3 g/L and acetic acid content in evaporated water is 2.8 g/L. The steam condensate does not contain any organic acid.

Using method of preferred embodiment 1, seed culture medium is prepared from tap water, evaporated water, and steam condensate respectively for aerobic cultivation. The fermentation culture medium is prepared from tap water. Results of fermentation are given in Table 1.

TABLE 1

Effects of separation process water for seed cultivation on fermentation results

| Seed culture medium | Fermentation culture medium | Initial glucose (g/L) | Succinic acid (g/L) | Acetic acid (g/L) | Succinic acid yield % |
|---|---|---|---|---|---|
| Tap water | Tap water | 20 | 15.06 | 1.53 | 85 |
| Evaporated water | Tap water | 20 | 16.72 | 1.34 | 92.8 |
| Steam condensate | Tap water | 20 | 15.12 | 1.63 | 84 |

It can be seen from Table 1 that when evaporated water is used for cultivation in aerobic stage, succinic acid concentration and yield reach the highest, i.e. 16.72 g/L and 92.8% respectively.

Embodiment 2

Aerobic cultivation of seed: Transfer germ seed from freezing storage tube to a test tube, and place this test tube in a mechanical shaker for overnight activation. Then, according to inoculum size of 1%, transfer the content of this test tube to a 500 mL conical flask containing 50 mL of seed culture medium. At temperature of 37° C. and shaker speed of 200 r/min, cultivate for 8 h.

Succinic acid production by thalli anaerobic fermentation in shake-flask: Carry out centrifugation of cultivated seed liquid at 4° C. and 8000 r/min for 10 min to obtain bacterial mud. Use sterilized water to wash this mud even and then transfer it to a 100 mL serum bottle containing 30 mL of liquid for anaerobic cultivation, so that initial concentration of thalli is 10 ($OD_{600}$). Then, connect $CO_2$ gas that has been filtered and sterilized for 2 min. Place it in a mechanical shaker at 37° C. and 200 r/min for anaerobic fermentation.

Preparation of evaporated water and steam condensate is synchronized with separation of succinic acid. Particular method is:

(1) Pre-filtering: pre-filtering, in particular micro-filtration, of succinic acid fermentation liquid is carried out to remove thalli and solid particles.

(2) Acidic ultrafiltration: adjust filtrate pH value to 6.0 for ultrafiltration, to remove biomacromolecules such as proteins. Operating temperature is 40° C. and operating pressure is 4.0 MPa. Collect ultrafiltration filtrate.

(3) Acidic nano-filtration: adjust ultrafiltration filtrate pH value to 4.0 for nano-filtration, to remove pigments, multivalence inorganic ions, and unconsumed substrate. Operating temperature is 40° C. and operating pressure is 2.5 MPa. Collect nano-filtration filtrate.

(4) Neutral nano-filtration: adjust pH value of nano-filtration filtrate containing succinic acid to 7.0 and repeat nano-filtration to remove byproducts such as formic acid and acetic acid, as well as mono-valence ions. Operating temperature is 40° C. and operating pressure is 4.0 MPa. Collect nano-filtration trapped liquid and realize pre-concentration.

(5) Concentration by evaporation: Perform concentration of nano-filtration trapped liquid by vacuum evaporation. Operating temperature is 75° C. and operating pressure is 0.1 MPa. Concentrated liquid is obtained, as well as large amount of evaporated water and steam condensate. Volume of evaporated water obtained is about ⅚ of the volume of succinic acid fermentation liquid. Keep the concentrated liquid at 70° C. and use sodium carbonate to adjust pH value of the concentrated liquid to 6.8. Next, perform crystallization by cooling, and drying, to obtain disodium succinate.

Detection of substances in evaporated water and steam condensate: HPLC has been used. Detection results: formic acid content in evaporated water is 1.0 g/L and acetic acid content in evaporated water is 2.5 g/L. The steam condensate does not contain any organic acid.

Using method of preferred embodiment 2, seed culture medium is prepared from tap water for aerobic cultivation. The fermentation culture medium is prepared from tap water, evaporated water, and steam condensate respectively for anaerobic fermentation. Results of fermentation are given in Table 2.

TABLE 2

Effect of separation process water for anaerobic fermentation on fermentation results

| Seed culture medium | Fermentation culture medium | Initial glucose (g/L) | Succinic acid (g/L) | Acetic acid (g/L) | Succinic acid yield % |
|---|---|---|---|---|---|
| Tap water | Tap water | 20 | 15.06 | 1.53 | 85 |
| Tap water | Evaporated water | 20 | 15.86 | 1.45 | 88 |
| Tap water | Steam condensate | 20 | 15.24 | 1.51 | 84.6 |

It can be seen from Table 2 that when evaporated water generated during separation is used for anaerobic fermentation, the result is the best. Since the steam condensate does not contain organic acid, and its compositions are the same as those of distilled water, it has no apparent effect on fermentation results.

Embodiment 3

Aerobic cultivation of seed: Transfer germ seed from freezing storage tube to a test tube, and place this test tube in a mechanical shaker for overnight activation. Then, according to inoculum size of 1%, transfer the content of this test tube to a 500 mL conical flask containing 50 mL of seed culture medium. At temperature of 37° C. and shaker speed of 200 r/min, cultivate for 8 h.

Succinic acid production by cultivation in anaerobic fermenter: according to inoculum size of 5%, transfer cultivated seed liquid to a 7 L fermenter (BioFlo 110 fermenter; New Brunswick Scientific Co., Edison, N.J.) containing 4 L of fermentation medium. Maintain fermentation temperature at 37° C. and use NaOH to adjust pH value to 7.0. At start of fermentation, connect 0.5 L/min of air and stir at 300 r/min. When thalli growth $OD_{600}$ value exceeds 5, start to connect oxygen enriched air. Adjust rotation speed so that DO≥30%. When thalli concentration reaches 15 ($OD_{600}$), start to use glucose makeup at limited speed to control thalli specific growth rate at about 0.07 $h^{-1}$, till thalli concentration reaches 30 ($OD_{600}$), at which time connection of $CO_2$ shall start, converting to anaerobic fermentation, at speed of 200 r/min. Use $NaCO_3$ to adjust pH value to 6.6.

Preparation of evaporated water and steam condensate is synchronized with separation of succinic acid. Particular method is:

(1) Pre-filtering: pre-filtering, in particular micro-filtration, of succinic acid fermentation liquid is carried out to remove thalli and solid particles.

(2) Acidic ultrafiltration: adjust filtrate pH value to 4.8 for ultrafiltration, to remove biomacromolecules such as proteins. Operating temperature is 30° C. and operating pressure is 3.0 MPa. Collect ultrafiltration filtrate.

(3) Acidic nano-filtration: adjust ultrafiltration filtrate pH value to 3.6 for nano-filtration, to remove pigments, multi-valence inorganic ions, and unconsumed substrate. Operating temperature is 35° C. and operating pressure is 2.0 MPa. Collect nano-filtration filtrate.

(4) Neutral nano-filtration: adjust pH value of nano-filtration filtrate containing succinic acid to 6.5 and repeat nano-filtration to remove byproducts such as formic acid and acetic acid, as well as mono-valence ions. Operating temperature is 30° C. and operating pressure is 3.0 MPa. Collect nano-filtration trapped liquid and realize pre-concentration.

(5) Concentration by evaporation: Perform concentration of nano-filtration trapped liquid by vacuum evaporation. Operating temperature is 70° C. and operating pressure is 0.05 MPa. Concentrated liquid is obtained, as well as large amount of evaporated water and steam condensate. Volume of evaporated water obtained is about ⅚ of the volume of succinic acid fermentation liquid. Keep the concentrated liquid at 60° C. and use sodium carbonate to adjust pH value of the concentrated liquid to 6.8. Next, perform crystallization by cooling, and drying, to obtain disodium succinate.

Detection of substances in evaporated water and steam condensate: HPLC has been used. Detection results: formic acid content in evaporated water is 1.7 g/L and acetic acid content in evaporated water is 2.9 g/L. The steam condensate does not contain any organic acid.

Figure 2:
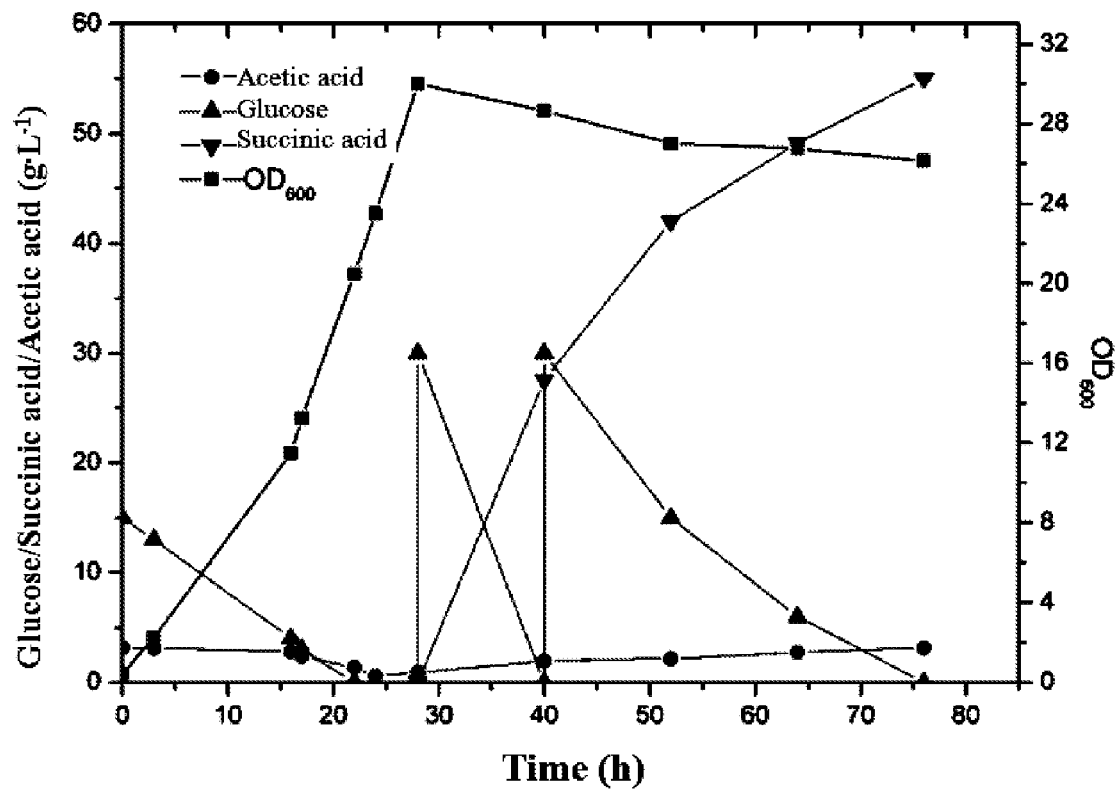
FIG. 2 Curves of change of concentrations of glucose, succinic acid, acetic acid, and thalli during cultivation of *Escherichia coli* AFP111 in JSM fermentation culture medium prepared from evaporated water generated during recovery of succinic acid.

In preferred embodiment 3, FIG. 1 and FIG. 2 show fermentation process curves of fermentation in 7 L fermenter using fermentation medium prepared from tap water and evaporated water generated during separation of succinic acid respectively.

It can be seen from FIG. 1 and FIG. 2 that final succinic acid concentration is 50.7 g/L by fermentation using culture medium prepared from tap water, and 55 g/L by fermentation using culture medium prepared from evaporated water, being an increase of 8.5%. Production intensity is 1.05 $g/L·h^{-1}$ and 1.13 $g/L·h^{-1}$ respectively. It is known from fermentation results that when succinic acid fermentation adopts culture medium prepared from evaporated water generated during succinic acid separation, both final succinic acid output and production intensity increase to some extent.

What is claimed is:

1. A method of cyclic utilization of water from a succinic acid production process, comprising step (a) which is recovering separately an amount of evaporated water and an amount of steam condensate from said succinic acid production process, step (b) which is using said evaporated water to prepare a first culture medium and conducting aerobic cultivation of seed in said first culture medium and step (c) which is using said steam condensate to prepare a second culture medium and conducting anaerobic fermentation in said second culture medium, said step (a) comprising a step of collecting an amount of fermentation liquor after anaerobic fermentation in said succinic acid production process, a step of treating said fermentation liquor in which said fermentation liquor is subject to pre-filtering, ultrafiltration under an acidic condition, nano-filtration under an acidic condition, and repeating of nano-filtration under a neutral condition, and a step of vacuum evaporation and concentration of said treated fermentation liquor to obtain succinic acid, evaporated water and steam condensate.

2. The method according to claim 1, wherein (1) said pre-filtering is micro-filtration conducted to remove thalli and solid particles, (2) said ultrafiltration is conducted under a pH value between 4.0~6.0, a temperature between 25~40° C., and a pressure between 0.2~4.0 MPa to remove biomacromolecules, (3) said nano-filtration is conducted under a pH value between 3.0~4.0, a temperature between 25~40° C., and a pressure between 1.0~2.5 MPa to remove pigments, multi-valence inorganic ions, and unconsumed substrate, (4) said repeating nano-filtration is conducted under a pH value between 6.0~7.0, a temperature between 25~40° C., and a pressure between 0.2~4.0 MPa to remove byproducts including formic acid and acetic acid, as well as mono-valence ions, and (5) said vacuum evaporation and concentration is conducted under a temperature between 65~75° C. and an operating pressure between −0.08~0.1 MPa.

* * * * *